(12) United States Patent
Jones et al.

(10) Patent No.: US 6,420,625 B1
(45) Date of Patent: Jul. 16, 2002

(54) BREATHABLE, LIQUID-IMPERMEABLE, APERTURED FILM/NONWOVEN LAMINATE AND PROCESS FOR MAKING SAME

(75) Inventors: Billy R. Jones, Cumming; Robert L. Shaffer; Mark B. Majors, both of Marietta, all of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/928,787

(22) Filed: Sep. 12, 1997

(51) Int. Cl.[7] .............................. A61F 13/15; B32B 3/10
(52) U.S. Cl. ...................... 604/367; 604/383; 428/138
(58) Field of Search .............................. 604/367, 383, 604/370; 428/131–137, 138, 139, 140, 170, 171, 172

(56) References Cited

U.S. PATENT DOCUMENTS

| | | |
|---|---|---|
| 3,073,303 A | 1/1963 | Schaar |
| 3,293,104 A | 12/1966 | Hartmann |
| 3,502,763 A | 3/1970 | Hull |
| 3,529,049 A | 9/1970 | Abell et al. |
| 3,542,634 A | 11/1970 | Such et al. |
| 3,654,060 A | 4/1972 | Goldman |
| 3,881,489 A | 5/1975 | Hartwell |
| 4,041,203 A | 8/1977 | Brock et al. |
| 4,196,245 A | 4/1980 | Kitson et al. |
| 4,306,559 A | 12/1981 | Nishizawa et al. |
| 4,341,216 A | 7/1982 | Obenour |
| 4,342,314 A | 8/1982 | Radel et al. |
| 4,485,133 A | 11/1984 | Ohtsuka et al. |
| 4,681,793 A | 7/1987 | Linman et al. |
| 4,690,679 A | 9/1987 | Mattingly, III et al. |
| 4,713,068 A | 12/1987 | Wang et al. |
| 4,755,413 A | 7/1988 | Morris |
| 4,758,239 A | 7/1988 | Yeo et al. |
| 4,759,754 A | 7/1988 | Korpman |
| 4,762,521 A | 8/1988 | Roessler et al. |
| 4,766,029 A | 8/1988 | Brock et al. |

(List continued on next page.)

OTHER PUBLICATIONS

Derwent Publications, Ltd., JA 6092057, Jul. 25, 1981 (Abstract).

(List continued on next page.)

FOREIGN PATENT DOCUMENTS

| | | |
|---|---|---|
| AU | 7336191 | 9/1991 |
| DE | 2517790 | 11/1976 |
| DE | 4407808 A1 | 9/1995 |
| EP | 0321980 A2 | 6/1989 |
| GB | 1367959 | 9/1974 |
| GB | 2076741 A | 12/1981 |
| GB | 2186233 A | 8/1987 |
| WO | 9424354 | 10/1994 |
| WO | 9516562 | 6/1995 |
| WO | 9619346 | 6/1996 |
| WO | 9639109 | 12/1996 |
| WO | WO9719803 | 6/1997 |

*Primary Examiner*—John G. Weiss
*Assistant Examiner*—Jamisue Webb
(74) *Attorney, Agent, or Firm*—Nelson Mullins Riley & Scarborough

(57) ABSTRACT

A breathable, liquid-impermeable, apertured film/nonwoven laminate is provided for use as a backsheet on various absorbent articles such as diapers, sanitary napkins, incontinent garments, and the like. The laminate is formed from a nonporous, breathable polymeric film layer, an apertured film layer, and a nonwoven web layer. The layers may be attached in an arrangement where the breathable polymeric film layer is sandwiched between the nonwoven web layer and apertured film layer, or where the apertured film layer is sandwiched between the nonwoven web layer and the breathable film layer. A process for making the laminate is also provided.

20 Claims, 4 Drawing Sheets

U.S. PATENT DOCUMENTS

| | | |
|---|---|---|
| 4,781,962 A | 11/1988 | Zamarripa et al. |
| 4,798,604 A | 1/1989 | Carter |
| 4,818,600 A | 4/1989 | Braun et al. |
| 4,820,294 A | 4/1989 | Morris |
| 4,828,556 A | 5/1989 | Braun et al. |
| 4,880,592 A | 11/1989 | Martini et al. |
| 4,898,761 A | 2/1990 | Dunaway et al. |
| 4,908,251 A | 3/1990 | Iimura et al. |
| 4,919,999 A | 4/1990 | Van Soom |
| 4,935,271 A | 6/1990 | Schirmer |
| 4,935,276 A | 6/1990 | Pawlowski et al. |
| 5,019,062 A | 5/1991 | Ryan et al. |
| 5,110,677 A | 5/1992 | Barmore et al. |
| 5,135,521 A | 8/1992 | Luceri et al. |
| 5,248,309 A | 9/1993 | Serbiak et al. |
| 5,261,899 A | 11/1993 | Visscher et al. |
| 5,264,268 A | 11/1993 | Luceri et al. |
| 5,296,291 A | 3/1994 | Mueller |
| 5,368,910 A * | 11/1994 | Langdon .................... 428/137 |
| 5,387,209 A | 2/1995 | Yamamoto et al. |
| 5,415,640 A | 5/1995 | Kirby et al. |
| 5,464,688 A | 11/1995 | Timmons et al. |
| 5,533,991 A | 7/1996 | Kirby et al. |
| 5,536,555 A | 7/1996 | Zelazoski et al. |
| 5,558,658 A | 9/1996 | Menard et al. |
| 5,560,974 A | 10/1996 | Langley |
| 5,591,510 A | 1/1997 | Junker et al. |
| 5,607,798 A | 3/1997 | Kobylivker et al. |
| 5,643,240 A | 7/1997 | Jackson et al. |
| 5,733,251 A * | 3/1998 | Johns |
| 6,117,523 A * | 9/2000 | Sugahara .................... 428/134 |

OTHER PUBLICATIONS

Derwent Publications, Ltd., JA 0199658, Dec. 7, 1982 (Abstract).

Derwent Publications, Ltd., JA 2148538, Jul. 2, 1987 (Abstract).

Derwent Publications, Ltd., DE 004123715, Feb. 20, 1992 (Abstract).

* cited by examiner

BREATHABLE, LIQUID-IMPERMEABLE, APERTURED FILM/NONWOVEN LAMINATE AND PROCESS FOR MAKING SAME

FIELD OF THE INVENTION

The present invention relates generally to materials useful in forming barriers that are impervious to liquids. Such materials are often used as outer covers or baffles for disposable diapers, sanitary napkins, incontinent pads, and other products where a liquid-impervious barrier may be desired. More specifically, the present invention relates to a composite material formed from a breathable film, an apertured film, and a non-woven substrate, as well as the process for making such composite material.

BACKGROUND OF THE INVENTION

Absorbent articles and products such as disposable diapers, sanitary napkins, bedpads, pantiliners, training pants, incontinent pads and garments, and the like, are items designed to be worn or placed adjacent to the body to absorb discharged bodily fluids. Bodily fluids absorbed by such products include urine, blood, menses and other excrements discharged by the body at various times.

Typically, such products are multilayered in construction and have a liquid-permeable cover, a liquid-impermeable baffle, and an absorbent material positioned in between the liquid-permeable cover and liquid-impermeable baffle. The liquid-permeable cover is designed to allow rapid transfer of bodily fluids into the absorbent layer(s) where the fluids can be retained. The baffle, which is usually an outer cover but may in some cases be positioned internally in the product, prevents leakage of the liquid retained within the absorbent area of the product. If the baffle were absent, leakage of the absorbed liquid could result in soiling of clothing, bedding, furniture, and other items positioned close to the absorbent article.

For many years, liquid-impermeable plastic films, such as polyethylene and polypropylene films, have been used to form the outer covers and baffles. Generally, such plastic films are impermeable to gases and water vapor, as well as liquids. The films prevent, or at least minimize, leakage by establishing a barrier to the passage of liquid from the absorbent article in situations where either the capacity of the absorbent article has been exceeded or the loading of the target zone has exceeded the capacity of the absorbent article to wick liquid from that target zone to liquid storage areas.

While completely liquid-impermeable films are well-suited to prevent the migration of liquid waste from the absorbent materials to the outer clothing of persons wearing such absorbent articles, the use of such liquid- and vapor-impermeable covers can result in a relatively high degree of humidity being maintained in the article when liquid has been absorbed. Oftentimes, a clammy feeling may result from this retained humidity. Such resulting clamminess also may contribute to skin irritations such as rashes if the article is left on a wearer for an extended period of time. In addition, due to the complete impermeability of such covers, the absorbent articles often feel hot to the user before being insulted with fluids.

Such completely impermeable films have been replaced in certain products with breathable, liquid-impermeable barriers. As used herein, the term "breathable" means that the barrier or film is pervious to water vapor and gases. In other words, "breathable barriers" and "breathable films" allow water vapor and gases to pass therethrough, but not necessarily liquids.

In some cases, breathable, liquid-impermeable barriers are made from various nonporous breathable films which, because of their molecular structures, are impervious to liquid but not impervious to vapors. These types of breathable barriers are generally composed of sufficient amounts of polymers such as poly(vinyl alcohol) ("PVOH"), polyvinyl acetate ("PVA"), ethylene vinyl alcohol ("EVA"), polyurethane, ethylene methyl acrylate ("EMA"), and ethylene methyl acrylic acid ("EMM") to make them breathable.

One such breathable, liquid-impermeable barrier is disclosed in U.S. Pat. No. 4,828,556 to Braun et al. Braun et al. is commonly owned by the assignee of the present invention and is incorporated herein in its entirety by reference. The breathable barrier of Braun et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, i.e., nonporous, meaning that it is substantially free of voids which connect the upper and lower surfaces of the film.

In other cases, breathable films are constructed with micropores therein to provide desired levels of liquid impermeability and vapor permeability. The micropores form what is often referred to as tortuous pathways through the film. Liquid contacting one side of the film does not have a direct passage through the film. Instead, a network of microporous channels in the film prevents liquids from passing, but allows gases and water vapor to pass. Due to their structure, such films are termed for purposes of the present application as "porous".

In some of such products, the breathable, liquid-impermeable barriers are made from polymer films that are highly filled with a substance such as calcium carbonate. The films are made breathable by stretching the filled films to create the microporous passageways as the polymer breaks away from the calcium carbonate during stretching.

Such porous breathable films are obviously more expensive to construct. In addition, porous breathable films are more susceptible to possible liquid penetrations than are nonporous breathable films.

An example of a breathable, yet fluid penetration-resistant material is described in U.S. Pat. No. 5,591,510 to Junker et al. The fabric material described in Junker et al. comprises a breathable outer layer of paper stock and a layer of breathable, fluid-resistant nonwoven material. The fabric also includes a thermoplastic film having a plurality of perforations which allow the film to be breathable while resisting direct flow of liquid therethrough.

Another breathable film barrier is disclosed in U.S. patent application Ser. No. 08/169,826 to McCormack. McCormack is also commonly owned by the assignee of the present invention and is incorporated herein in its entirety by reference. (The published PCT application that corresponds to this United States patent application is WO 95/16562, published on Jun. 22, 1995.) As disclosed therein, a breathable film is adhered to a fibrous polyolefin nonwoven web to form a breathable, cloth-like film/nonwoven composite. In particular, McCormack discloses a bonding agent incorporated into one or more layers of the composite which makes the layers easier to thermally bond into a composite.

Another film/nonwoven laminate is disclosed in U.S. patent application Ser. No. 08/359,987 to McCormack et al.

This application is also commonly owned by the assignee of the present invention and is incorporated herein in its entirety by reference. (The PCT application corresponding to this United States patent application was published on Jun. 27, 1996, under WO 96/19346.) McCormack et al. discloses a low gauge, multilayer film, which may be laminated to other materials such as, for example, fibrous nonwoven webs. In particular, the films have a core layer made from an extrudable thermoplastic polymer and then has one or more skin layers attached to the exterior surfaces of the core layer. In some instances, the multilayer films are made breathable either through the use of specialized polymers which permit diffusion of gases through the layer and/or through the use of particulate fillers.

Other designs of breathable absorbent articles include diapers that are arranged to provide some level of breathability at the leg cuff regions of the diaper, articles that have humidity transfer regions in the form of breathable panels in otherwise vapor-impermeable outer covers, and articles having perforated regions to help the garment breath. An example of an absorbent article having a humidity transfer area is shown in U.S. Pat. No. 5,558,658 to Menard et al. This patent utilizes a liquid- and vapor-impermeable backsheet in some embodiments and a liquid-impermeable, vapor-permeable backsheet in others. Menard et al. is owned by the assignee of the present invention and is incorporated herein in its entirety by reference.

U.S. Pat. No. 4,681,793 to Linman et al. describes an absorbent article such as a diaper or sanitary napkin which utilizes a liquid-impervious backsheet. The backsheet is made from an inner layer which is provided next to an absorbent layer and an outer layer which forms the side of the article which will be farthest from the wearer's body. The inner layer may be constructed from a substantially liquid- and vapor-impervious polymeric film such as polyethylene or from a substantially liquid-impervious, but vapor-pervious material such as a porous polytetrafluoroethylene. Linman et al. specifically notes that the uses of such porous liquid-impervious, vapor-pervious materials are more expensive than using liquid- and vapor-impervious films. The outer layer of the backsheet in this arrangement comprises a layer of polymeric film that has a number of relatively small, protuberances, each exhibiting a tiny aperture at its apex.

U.S. Pat. No. 4,341,216 to Obenour describes a two-element breathable backsheet for use on disposable diapers. The inner panel which is adjacent to the diaper's absorbent material is made from a liquid impermeable film such as polyethylene. The outer panel is constructed so that it includes liquid- and vapor-impermeable regions as well as liquid-impermeable, vapor-pervious regions. In an alternative embodiment, Obenour states that the inner panel includes a liquid-impermeable region as well as liquid- and vapor-pervious regions. In this embodiment, the liquid- and vapor-pervious regions are preferably perforated so as to allow vapor and liquid passage.

On the other hand, the body-facing side of such absorbent articles have been designed so that they are liquid-permeable. Obviously, the side of the absorbent article facing the body should allow for quick and efficient passage of the bodily fluids into the absorbent material layer(s). For example, U.S. Pat. No. 4,690,679 to Maftingly. III et al. describes the use of an absorbent material sealed between a fluid impervious barrier and an apertured film cover. The apertured film cover described therein comprises a two-layer apertured film formed by the coextrusion of two polymers. The film is "apertured" in that it includes a plurality of apertures that extend from the upper surface of the film to the lower surface of the film.

Although various designs of backsheets for absorbent articles are known in the art, the presently available backsheets do not allow breathability in the manner provided by the present invention. In particular, the art is generally deficient in providing a liquid-impervious, but vapor-pervious backsheet designed to provide cloth-like aesthetics, with relatively high bulk at a relatively low cost.

SUMMARY OF THE INVENTION

It is an object of the present invention to provide an improved backsheet for forming the outer cover of an absorbent article.

It is another object of the present invention to provide an absorbent article with an improved backsheet.

Another object of the present invention is to provide a liquid-impermeable, vapor-pervious backsheet for absorbent articles.

An additional object of the present invention is to provide a liquid-impermeable, vapor-pervious backsheet for absorbent articles that exhibits certain desirable aesthetic characteristics.

Another object of the present invention is to provide a process for making a liquid-impermeable, vapor-pervious laminate that is apertured and useful as the backsheet for absorbent articles.

These and other objects are achieved by providing a breathable (vapor-pervious), liquid-impermeable apertured film/nonwoven laminate. The laminate comprises at least three layers: a nonwoven, an apertured film, and a breathable, nonporous, but liquid-impervious, film. The layers may be arranged in any sequence, meaning that the apertured film layer may be sandwiched between the breathable film layer and the nonwoven layer or the breathable film layer may be sandwiched between the apertured film layer and the nonwoven.

The nonwoven may comprise any nonwoven material and may advantageously be a spunbond, meltblown, or spunbond/meltblown spunbond material. The nonwoven may comprise single component fibers or bicomponent fibers in, for example, a sheath/core type arrangement or in a side-by-side arrangement.

The apertured film may be any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

The particular nonporous, breathable film may be varied and includes films of poly(vinyl alcohol) ("PVOH"), polyvinyl acetate ("PVA"), ethylene vinyl alcohol ("EVA"), polyurethane, ethylene methyl acrylate ("AMA"), and ethylene methyl acrylic acid ("EMAA"). In addition, the breathable film may consist of mixtures of two or more breathable polymers or may be constructed from mixtures of nonbreathable polymers such as polyethylene and a sufficient amount of breathable polymer to provide the overall film with sufficient vapor-permeability characteristics to make it classifiable as breathable.

In forming the breathable film/nonwoven laminate, the desired layers may be bonded together in a number of various ways.

Thermal bonding, adhesive bonding, and sonic bonding are merely examples of various bonding techniques that may be utilized in the present process to attach either the apertured film layer or the breathable film layer to the nonwoven. The breathable film layer may be attached to the apertured film layer in various ways, including extrusion coating, thermally laminating, adhesively laminating, and sonically bonding.

The apertured film may be used in a thicknesses of from about 4 mils to about 40 mils, with such thickness being determined after the apertured film is formed. The breathable film layer will typically be used in thicknesses of from about 0.01 mils to about 5 mils. The nonwoven web layer will typically have a basis weight of from about 0.25 ounces per square yard (osy) to about 5.0 osy.

In use, the backsheet described herein may be utilized as the outer cover on a number of various absorbent articles. Such absorbent articles include disposable diapers, sanitary napkins, bedpads, pantiliners, training pants, incontinent pads and garments, and the like. The backsheet may be arranged on the absorbent article in any orientation, but preferably will be attached so that the nonwoven layer faces outward and is in contact with the clothing of the wearer and the apertured film and breathable film layers face inward towards the absorbent core of the absorbent article, Other objects, features and aspects of the present invention are discussed in greater detail below.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures, in which.

Figure 1:
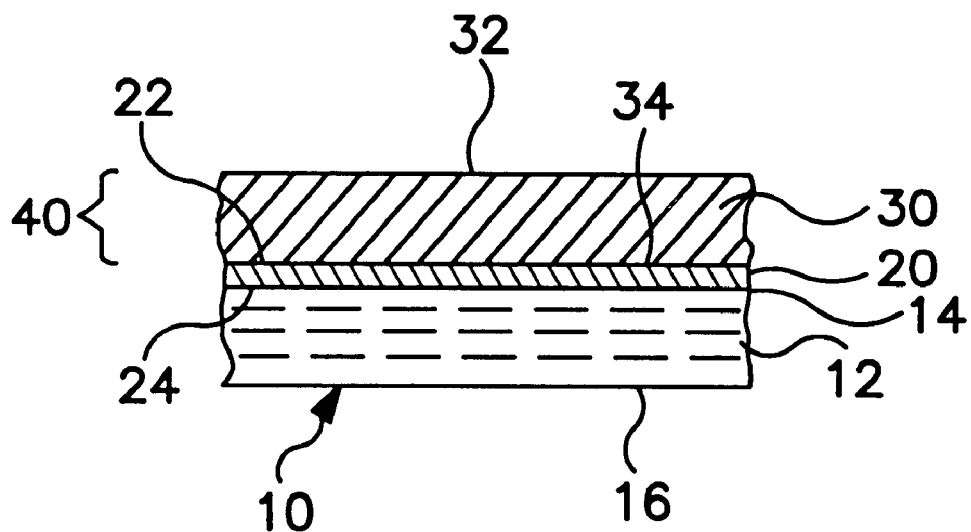
FIG. 1 is a diagrammatic representation of a cross-sectional view of the breathable, liquid-impermeable, apertured film/nonwoven laminate of the present invention.

Repeat use of reference characters in the present specification and drawings is intended to represent the same or analogous features or elements of the invention.

DETAILED DESCRIPTION OF PREFERRED EMBODIMENT

It is to be understood by one of ordinary skill in the art that the present discussion is a description of exemplary embodiments only and is not intended as limiting the broader aspects of the present invention, which broader aspects are embodied in the exemplary construction.

The present invention addresses the objectives and needs discussed above by providing a breathable, liquid-impermeable, apertured film/nonwoven laminate material formed from a nonwoven layer, an apertured film layer, and a nonporous, breathable film layer. The layers may be arranged so that the apertured film layer or the breathable film layer is attached to the nonwoven layer. The laminate material is particularly useful for forming a liquid-impermeable, vapor-pervious backsheet for various absorbent articles such as diapers, sanitary napkins, incontinent garments, and the like.

FIG. 1 shows one embodiment of the present inventive laminate. The laminate 10 comprises a nonwoven web layer 12 having a first surface 14 and a second surface 16. A laminate layer 40 comprising a breathable film layer 20 having a first surface 22 and a second surface 24 and an apertured film layer 30 having a first surface 32 and a second surface 34 is attached via breathable film layer 20 as described below to the first surface 14 of nonwoven web layer 12. The figures do not necessarily show apertures of any particular shape or diameter through the apertured film layer 30. It is to be understood that a number of the apertures through apertured film layer 30 extend from one surface of apertured film layer 30 to the other surface of apertured film layer 30, and may be of any desired shape and any desired diameter.

Figure 2:
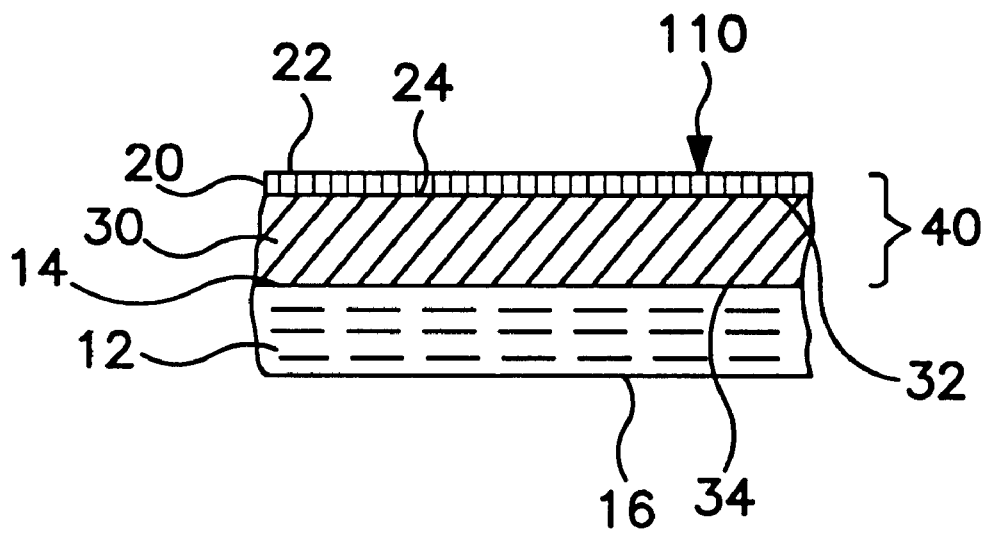
FIG. 2 is a diagrammatic representation of a cross-sectional view of an alternative embodiment of the breathable, liquid-impermeable, apertured film/nonwoven laminate of the present invention.

In FIG. 1, first surface 22 of breathable film layer 20 is attached to the second surface 34 of apertured film layer 30 and second surface 24 of breathable film layer 20 is attached to the first surface 14 of nonwoven web layer 12 so that breathable film layer 20 is sandwiched between nonwoven web layer 12 and apertured film layer 30. Alternatively, the layers may be arranged as shown in FIG. 2 wherein laminate 110 has the first surface 32 of apertured film layer 30 attached to second surface 24 of breathable film layer 20 and second surface of apertured film layer 30 attached to first surface 14 of nonwoven web layer 12 so that apertured film layer 30 is sandwiched between nonwoven web layer 12 and breathable film layer 20.

Either arrangement of laminate material 10 or laminate material 110 is suitable for use in the present applications. As explained, the laminate material is useful as the backing sheet, or backsheet, of various disposable absorbent articles.

Figure 3:
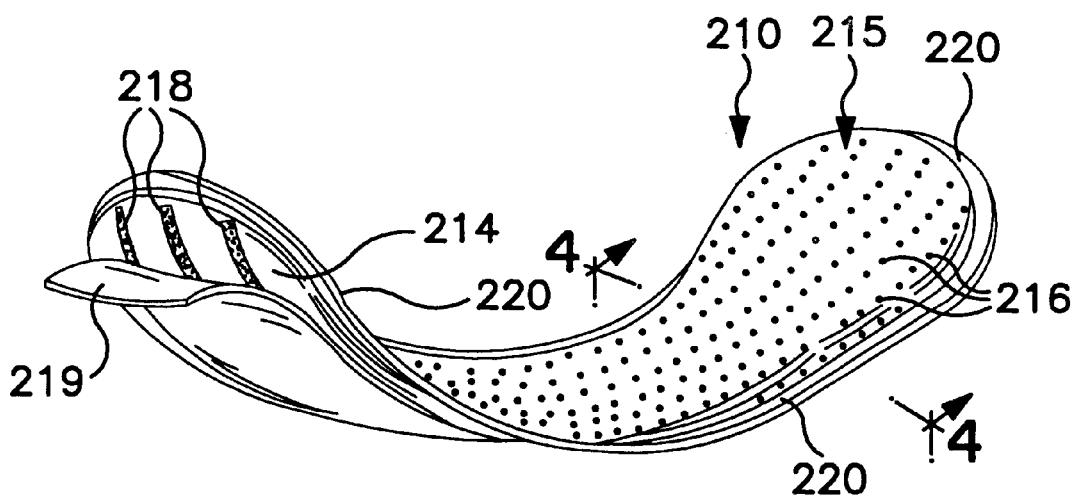
FIG. 3 is a plan view of a sanitary napkin as a representative absorbent article utilizing the present breathable, liquid-impermeable, apertured film/nonwoven laminate as a backsheet.

An example of one particular absorbent article for which the present inventive laminate material may be used is shown in FIG. 3. FIG. 3 illustrates a sanitary napkin 210 having a liquid permeable top sheet 215 that may be thermally bonded to a backsheet 214 about the periphery 220 of sanitary napkin 210. Longitudinally extending pressure sensitive adhesive strips 218 may be disposed on the garment-facing side of backsheet 214. These adhesive strips 218 are for attaching the sanitary napkin 210 to the crotch portion of an undergarment. Overlying the adhesive strips 218 is a protective release strip 219 which is provided to protect the adhesive strips 218 from dirt and unintended adhesion prior to use.

Figure 4:
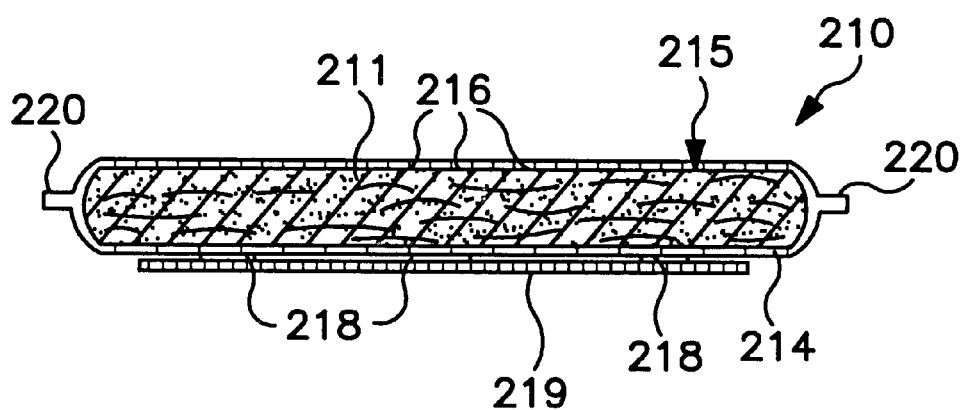
FIG. 4 is a cross-sectional view of the sanitary napkin of FIG. 3 taken along line 4—4.

As shown in FIG. 4, which is a cross-section of sanitary napkin 210 along line 4—4 in FIG. 3, an absorbent core 211 is sealed between backsheet 214 and liquid permeable top sheet 215. Liquid permeable top sheet 215 will typically have numerous apertures 216 running therethrough to allow bodily fluids to pass easily to absorbent core 211.

The sanitary napkin shown in FIGS. 3 and 4 is meant only to be representative of the various types of absorbent articles on which the present inventive liquid-impermeable, vapor-pervious laminate may be used as a backsheet. Any of the various absorbent articles, such as diapers, incontinent devices, bedpads, and the like, which would benefit from having a liquid-impermeable, vapor-pervious backsheet may employ the present laminate. The making of such articles utilizing backsheets employing the present laminate is well within the skill of those in the art.

As used herein, the terms "nonwoven layer" and "nonwoven web" refer to webs having a structure of individual fibers or threads that are interlaid, but not in a regular, repetitive manner as in a knitted fabric. Nonwovens are preferred in the present invention because they add clothlike aesthetics to the backsheet at a lower cost than typical knitted fabrics.

Nonwoven fabrics or webs may be formed from many processes such as for example, meltblowing processes, spunbonding processes, conforming processes, spunbonding/meltblowing/spunbonding processes and bonded carded web processes. Amounts and thicknesses of nonwoven fabrics is generally based on the basis weight of the fabric. Basis weights are usually expressed in ounces of material per square yard (osy) or grams per square meter (gsm) and fiber diameters are usually expressed in microns. (To convert from osy to gsm, a multiplication factor of 33.91 is used.)

Meltblown fibers are formed by extruding a molten thermoplastic material through a plurality of fine, usually circular, die capillaries as molten threads or filaments into converging high velocity gas (e.g., air) streams which attenuate the filaments and reduce their diameter. Meltblown fibers are generally smaller than 10 microns in diameter. After formation, the meltblown fibers are carried by the high velocity gas stream and are deposited on a collecting surface to form a web of randomly disbursed meltblown fibers. The formation of meltblown materials is demonstrated by NRL Report 4364, "Manufacture of Super-Fine Organic Fibers," by V. A. Wendt, E. L. Boon, and C. D. Fluharty; and NRL Report 5265, "An Improved Device for the Formation of Super-Fine Thermoplastic Fibers", by K. D. Lawrence, R. T. Lukas, and J. A. Young. By way of example, a meltblowing process that may be used in making the nonwoven web for use in the present invention is described in U.S. Pat. No. 3,849,241 to Buntin et al., which is incorporated herein in its entirety by reference.

The nonwoven layer of the present laminate may be also be a spunbond web of material. Spunbonded fibers are small diameter fibers formed by extruding molten thermoplastic materials as filaments from a plurality of fine, usually circular, capillaries of a spinnerefte with the diameter of the extruded filaments then being rapidly reduced by, for example, non-eductive or eductive fluid-drawing or other spunbonding mechanisms. Spunbond fibers are generally continuous and larger than 7 microns in diameter, and usually between about 10 and 20 microns in diameter. Spunbonding processes are described in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,502,763 to Hartman, U.S. Pat. No. 3,341,394 to Kinney, U.S. Pat. No. 3,502,763 to Levy, U.S. Pat. No. 3,909,009 to Levy, and U.S. Pat. No. 3,542,615 to Dobo et al., all of which are incorporated herein in their entireties by reference.

The nonwoven layer of the present inventive laminate may also be a spunbond/meltblown/spunbond, or SMS, material. A typical SMS material is described in U.S. Pat. No. 4,041,203 to Brock et al. which is incorporated herein in its entirety by reference. Other SMS products and processes are described for example in U.S. Pat. No. 5,464,688 to Timmons et al., U.S. Pat. No. 5,169,706 to Collier et al. and U.S. Pat. No. 4,766,029 to Brock et al., all of which are also incorporated herein in their entireties by reference. Generally, an SMS material will consist of a meltblown web sandwiched between two exterior spunbond webs. Such SMS laminates have been available commercially for years from Kimberly-Clark Corporation under marks such as Spunguard® and Evolution®. The spunbonded layers on the SMS laminates provide durability and the internal meltblown barrier layer provides porosity and additional cloth-like feel.

Additional references which add to the teachings of performing processes of meltblowing, spunbonding, and conforming include U.S. Pat. Nos. 3,016,599, 3,755,527, 3,704,198, and 4,100,324, all of which are incorporated herein in their entireties by reference.

Bonded carded webs are made from staple fibers which are usually purchased in bales. The bales are placed in a picker which separates the fibers. The fibers are then sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed through the web and then activated, usually by heating the web and adhesive with hot air. Another bonding method is pattern bonding wherein heated calendar rolls or ultrasonic bonding equipment is used to bond the fibers together, usually in a localized bond pattern though the web can be bonded across its entire surface if so desired.

The nonwoven layer of the present invention, whether made from a spunbond, meltblown, SMS, or other material, will generally be composed of polymers such as, for example, polyamides, polyolefins, polyesters, polyvinyl alcohols, polyurethanes, polyvinyl chlorides, polyfluorocarbons, polystyrenes, caprolactams, poly (ethylene vinyl acetates), ethylene n-butyl acrylates, cellulosic and acrylic resins or copolymers and blends thereof. Polyolefins suitable for use in the nonwoven layer include polyethylene, e.g., high density polyethylene, medium density polyethylene, low density polyethylene and linear low density polyethylene; polypropylene, e.g., isotactic polypropylene, syndiotactic polypropylene, blends thereof, and blends of isotactic polypropylene and atactic polypropylene; polybutylene, e.g., poly(1-butene) and poly(2-butene); polypentene, e.g., poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Polyamides suitable for the webs include fibers made from nylon 6, nylon 6/6, nylon 4/6, nylon 11, nylon 12, nylon 6/10, nylon 6/12, nylon 12/12, copolymers of caprolactam and alkaline oxide diamine, and the like, as well as blends and copolymers thereof. Suitable polyesters include polyethylene terephthalate, polybutylene terephthalate, polytetramethylene terephthalate, polycyclohexylene-1,4-dimethylene terephthalate, and isophthalate copolymers thereof, as well as blends thereof.

In addition, bicomponent fibers may be used in forming the nonwoven web layer of the present laminate. Bicomponent fibers are formed from at least two polymers extruded from separate extruders but then are spun together to form one fiber. The configuration of such a bicomponent fiber may be, for example, a sheath/core arrangement wherein one polymer is surrounded by another, or may be a side-by-side arrangement as illustrated in U.S. Pat. No. 5,108,820 to Kaneko et al., or may be an "islands-in-the-sea" arrangement.

Biconstituent fibers may also used. Biconstituent fibers are formed from at least two polymers extruded from the same extruder as a blend. These fiber are sometimes referred to as multiconstituent fibers and usually have fibrils of one of the polymers within a matrix of the major polymer. Fibers of this general type are discussed in, for example, U.S. Pat. No. 5,108,827 to Gessner.

It is important to understand that any of the various nonwoven webs and methods for making nonwoven webs are useful in the present inventive laminate. The particular nonwoven web utilized will depend on the particular characteristics desired for the specific use of the backsheet into which the nonwoven web will be incorporated.

The breathable film layer 20 in the present inventive laminate may comprise any nonporous, polymeric film that is capable of being liquid-impermeable, but vapor-pervious. In other words, the film utilized for this layer must allow vapors such as water vapor and gases to pass therethrough, but prevent liquids from passing. As used herein, liquids are distinguished from vapors and gases in that liquids have typical easy flowability characteristics with little or no tendency to disperse whereas vapors are in a gaseous state or are suspended in a gaseous state and are readily dispersible. Obviously, vapors may become liquified with the addition of sufficient pressure.

The breathability of the breathable film layer 20, in combination with the apertured film layer 30, ensures that any backsheet formed from the present laminate will allow moisture in the form of vapors to escape into and out of the absorbent portion of the article. However, the breathable film layer 20 must be constructed so that liquids maintained within the absorbent core 211 of the article will not leak through the backsheet 214.

Various breathable films may be utilized in the present invention. One type of film that may be used is a nonporous, continuous film, which because of its molecular structure is capable of forming a vapor-pervious barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Although the inventors do not intend to be held to a particular mechanism of operation, it is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

The breathable film layer will typically be used in thicknesses of from about 0.01 mils to about 5 mils. More preferably, the thickness of the breathable film layer will be from about 0.01 mils to about 1.0 mils.

As used herein, the term "apertured" refers to a substrate which is porous as opposed to nonporous and specifically describes a film which has a number of holes or apertures connecting a first outer surface of the film with a second outer surface of the film. The apertures in apertured film allow liquids as well as vapors and gases to freely pass through the film.

In the present laminate, the use of an apertured film layer 30 adds depth and loft or bulk to the laminate without adding excessive cost. Most users of absorbent articles expect them to exhibit a certain bulk, or loft. Generally, the addition of bulk to an absorbent article increases the perception to the user that the article is capable of absorbing large amounts of liquids. The apertured film layer 30 accomplishes this by increasing the depth of the laminate in what is generally referred to as the z-direction (as opposed to the x- and y-directions which form the horizontal plane). Moreover, the apertured film provides for sufficiently large passageways to allow for good vapor transmission.

Finally, when the apertured film 30 is positioned between the breathable film layer 20 and the nonwoven web layer 12 as shown in FIG. 2, the apertured film acts as a spacer between the breathable film and nonwoven web layer to assist in reducing the amount of clamminess felt by the wearer of the absorbent article. This is accomplished by the apertured film drawing away condensation of water vapor that might form on the breathable film layer 20.

Any apertured polymeric film may be used in the present invention. Such apertured films may be mechanically apertured after formation or may be initially formed as a porous substrate.

Typically, the apertured film layer 30 may be made from any material which can be formed into a film, including, but not limited to, polyolefins and polyacrylates, as well as copolymers and blends thereof. Specific polymers include, but are not limited to, polyethylene, low density polyethylene, linear low density polyethylene, and ethylene vinyl acetate. If thermal bonding or sonic bonding is to be used for bonding the layers into a laminate, an apertured film should be chosen which can thermally or sonically bond to the breathable film layer.

Means for forming apertured films are well known. Casting and blowing of apertured films are two such examples. Apertured films suitable for use in the present laminate include AET polyethylene CKX215 film manufactured by Applied Extrusion Technology of Middleton, Del.; SULTEX PF-10 EVA/(LDPE/PP)IEVA film from Sultex SRL of Agliana, Italy and a Mitsui low density polyethylene film from Mitsui and Co., Ltd of Tokyo, Japan. The AET polyethylene CKX215 film has a percent open area of approximately 28%, the SULTEX PF-10 film has 18–22% open area and the Mitsui film as a 22–24% open area. (Open area is calculated by specifying a unit area, calculating the surface area of all open areas within the specified unit area, dividing the total open area by the total surface area within the specified unit area and then multiplying the quotient by 100 to yield percent open area.)

In addition, films may be mechanically apertured after formation. One method of mechanically aperturing a film is described in U.S. Pat. No. 4,820,294 to Morris, which is incorporated herein in its entirety by reference. As described in Morris, a supply of film is brought into pressure contact with a plurality of pins or needles mounted on a rotatable roll. The pins are then withdrawn from the film, leaving the desired apertures.

Other methods of aperturing films and other materials include the process of vacuum aperturing films described in U.S. Pat. No. 3,929,135 to Thompson; the process of aperturing meltblown nonwovens described in U.S. Pat. No. 4,469,734 to Minto; and the process of aperturing films and other substrates described in German Patent No. 26 14 160 to Endler and in European Patent Application No. 0 598 970 A1 to Giacometti.

Figure 5:
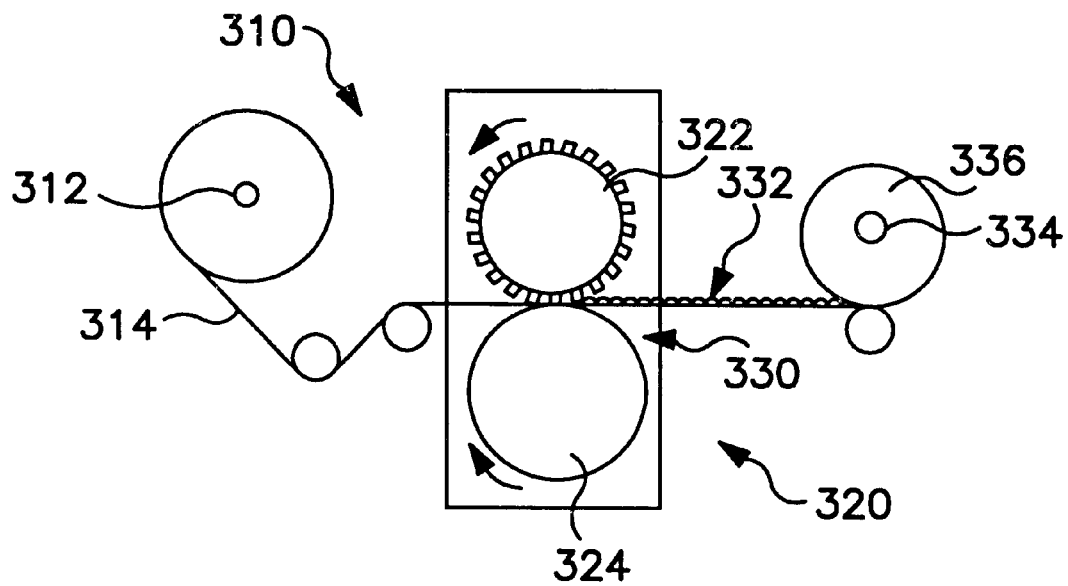
FIG. 5 is a schematic side view of a process and apparatus for aperturing the polymeric film that may be utilized in the present inventive laminate.

Alternatively, a process and apparatus utilized in the making of the apertured film described in Example 1 below may be employed for aperturing film. In this process as shown in FIG. 5, an apertured film 432 is made by subjecting an unapertured, continuous film 414 to the aperturing apparatus generally shown as element 410. The aperturing apparatus 410 includes a film unwind 412 for a film 414. In order to manipulate the properties of the apertured film formed in the process, it is advantageous to control the speed of the unwind 412. As a result, it is desirable to provide each of the unwinds with driving and/or braking means (not shown) to control the speed of the unwind. Such driving and/or braking means are widely known and commonly used in conjunction with such unwinds to control tension.

The continuous polymeric film 414 is unwound and passed into an aperturing assembly 420. The aperturing assembly 420 includes a pattern roll 422 and an anvil roll 424, both of which are driven and/or braked with respect to one another so as to create a speed differential between the two rolls 422 and 424. Suitable means for driving the pattern roll 422 and the anvil roll 424 include, for example, electric motors (not shown).

Figure 6:
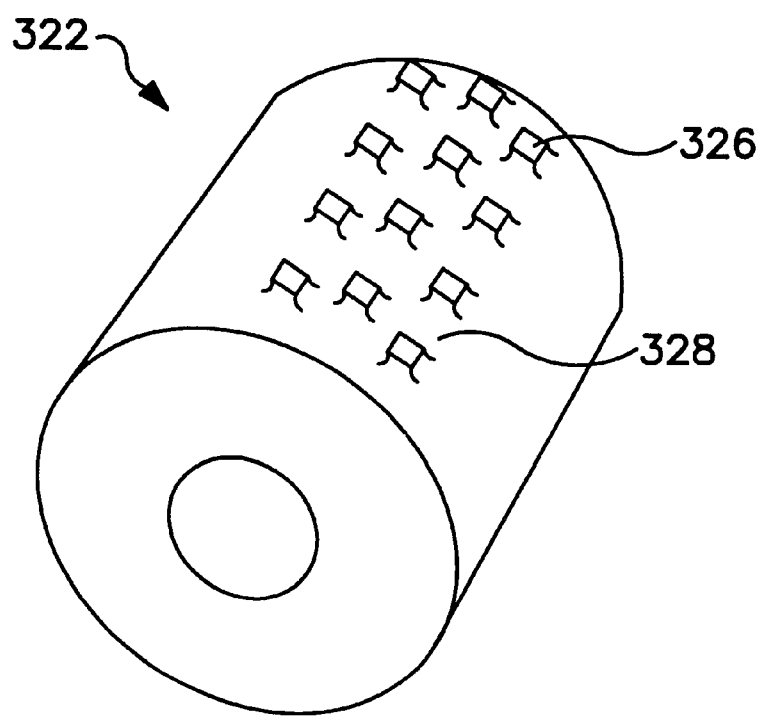
FIG. 6 is a partial perspective view of an exemplary pattern roll which may be used in the apparatus shown in FIG. 5 to construct the apertured film that may be utilized in the present inventive laminate.

The pattern roll 422 is typically made from a durable material such as steel. Pattern roll 422 will have a pattern of raised areas or protuberances 426 (shown in FIG. 6) separated by a pattern of depressed areas 428. Protuberances 426 are designed to contact the surface of anvil roll 424. The size, shape, pattern and number of protuberances 426 on the pattern roll 422 may be varied to meet the particular characteristics desired in the apertured film.

Anvil roll 424 is characterized in that its surface is much smoother than the pattern roll 422 and, preferably, is flat. Anvil roll 424, however, may exhibit a slight pattern and still be considered flat. For example, if the anvil roll is made from or has a softer surface than the pattern roll, such as a resin impregnated cotton or a rubber surface, it may develop irregularities yet will still be considered flat. Anvil roll 424 provides the base for the pattern roll 422 and film 414 to shear against. Typically, the anvil roll 424 will be made from steel or materials such as hardened rubber, resin-treated cotton, or polyurethane.

Both the pattern roll 422 and anvil roll 424 are provided with means (not shown) for heating their surfaces to desired temperatures. Heating and/or cooling can affect the features of the apertured film produced. Common heating means include hot oil and electrical resistance heating.

The anvil roll 424 and pattern roll 422 are counterrotated at differential speeds. The speeds are generally measured at the surfaces of the rolls and may be expressed as a ratio of pattern roll speed to anvil roll speed. In use, the pattern roll 422 will usually run at a faster speed than the anvil roll 424. However, in certain instances, it might be desirable to run the rolls at the same speed or run the anvil roll 424 faster than the pattern roll 422.

The position of the anvil roll 424 and pattern roll 422 with respect to each other may be varied to create a nip area 230 between the rolls. The nip pressure can be varied depending upon the properties of the web itself and the type of aperturing desired and is usually controlled by hydraulic cylinders (not shown) connected to the rolls. The nip pressure will generally range between about 2.0 to about 6.0 kilograms per lineal millimeter (kg/1 mm).

The differential speed and pressure between the pattern roll 422 and the anvil roll 424 cause a shear between the protuberances 426 on the pattern roll 422 and the surface on the anvil roll 424. This shearing action acts to score the film and create apertures therethrough.

As the apertured film 432 leaves aperturing assembly 420, it may then be collected on a film winder 434 to form a roll of apertured film 436. This winder 434, like the unwind 412, may be driven by an electric motor or other drive source which can be varied (not shown). The winding speed, like the unwind speed, might also affect the properties of the apertured film.

The particular apertured film and the process of making the film is not critical to the present inventive laminate. It is to be understood that any apertured film exhibiting the general characteristics of the exemplary apertured films described herein may be utilized in forming the laminate.

The apertured film may be used in thicknesses of from about 4 mils to about 40 mils and, more preferably, in thicknesses of from about 4 mils to about 25 mils. Even more preferably, the apertured film will have a thickness of from about 10 mils to about 20 mils. The thicknesses used herein are the thicknesses measured after the aperturing has been performed on the film. Prior to aperturing, the film will be relatively flat. After aperturing, the film will exhibit both flat areas ("lands") as well as protuberances ("cones"). The thickness measurements for the apertured film includes the height of both the flat areas coupled with the protuberances.

The absorbent body onto which the present inventive laminate may be attached as a backsheet may include any material that exhibits an absorbency for fluids. Typically, absorbent core 211 will include a pad composed of airlaid, cellulosic fibers commonly referred to as wood pulp fluff. Natural fibers, such as cotton, may also be employed. In addition, absorbent core 211 may include coformed material composed of a mixture of cellulosic fibers and synthetic polymers. For example, the coform material may be composed of an airlaid blend of cellulosic fibers and meltblown polyolefin fibers.

Absorbent core 211 may also include effective amounts of inorganic and/or organic high absorbency materials to enhance the absorptive capacity of the absorbent article. Inorganic superabsorbent materials include, for example, absorbent clays and silica gels. Organic superabsorbents include natural materials such as agar, pectin, guar gum and peat moss, as well as synthetic materials such as hydrogel polymers. Hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyvinyl pyridine, and the like. Such high absorbency materials are typically capable of absorbing at least 15 times their weights in water, and more typically, from about 25 to 50 times their weights in water.

The employment of an absorbent core in absorbent products such as diapers and sanitary napkins is well known and is described, for example, in U.S. Pat. Nos. 5,558,658 to Menard et al. and U.S. Pat. No. 5,248,309 to Serbiak et al., both of which are incorporated herein in their entireties by reference.

As mentioned above, a typical absorbent article will employ a liquid permeable top sheet 215 which will be positioned against the body when the absorbent device is in use. The top sheet should allow a relatively free passage of liquid therethrough to assist in maintaining a relatively dry surface against the wearer's skin. Typically, top sheet 215 will be composed of a porous nonwoven material, such as a spunbond material composed of polyolefin filaments. Suitable filaments include, for example, polyethylene and polypropylene filaments as described in U.S. Pat. No. 4,762, 521 to Roessler et al., which is incorporated herein in its entirety by reference. Alternatively, top sheet 215 may comprise an apertured film as described in U.S. Pat. No. 5,643,240 to Jackson et al., which is also incorporated herein in its entirety by reference.

In the process for forming the inventive laminate, the breathable polymeric film layer 20 is attached to apertured film layer 30 by any typical method of attaching one film to another. As described below in Examples 2–6, one method for attaching the breathable film to the apertured film is by directly extrusion coating the breathable film onto the apertured film. Ordinary extrusion coating equipment such as that described below may be employed for such purposes.

Other methods of attachment include thermal bonding where heat is used to effect the bonding between the films, adhesive bonding where an adhesive such as a latex is used to bond the films together, and sonic bonding where a sonic device is used to cause the a constituent in the films to activate and sonically bond together. The method of attaching the breathable film to the apertured film is not necessarily critical to the broad concept of the present laminate.

After the apertured film and nonporous, breathable film layers have been bonded together, the combined films are then brought into contact with the nonwoven web layer 12 for bonding thereto. As previously described and shown in FIGS. 1 and 2, either side of the combined apertured film/breathable film laminate may be bonded to the nonwoven web layer 12 in order to form the inventive breathable, liquid-impermeable, apertured film/nonwoven laminate. Typically, this bonding will be accomplished thermally by subjecting the product to heat and/or pressure sufficient to melt a portion of either or both of the nonwoven layer and apertured film/breathable film laminate. This process of thermal attachment using typical calendaring rolls is described below in Examples 7–11.

Other methods of bonding the nonwoven web with the combined apertured film and breathable film laminate include adhesive bonding and sonic bonding. Again, the particular method of bonding is not critical to the present invention, provided the polymers used in forming the films and the nonwoven webs are bonding-compatible.

In addition, the present invention does not depend on which side of the apertured film is attached to the breathable polymer film layer or the nonwoven layer. As is known, apertured film will typically have a side upon which the protuberances or cones exist (known as the "male side"), and a side that is generally flat except for the valleys or voids which form the underside of the protuberances (known as the "female side"). The apertured film in the present invention may be attached to the nonwoven on either its male or its female side and may be attached to the breathable polymer layer on either its female side or its male side.

One particular representative example of a breathable, apertured film/nonwoven laminate according to the present invention consists of a mechanically apertured polyethylene film with a basis weight of 50 gsm that is extrusion coated with 15 gsm or less of a breathable EVA polymer film layer having a 28% vinyl alcohol content. The breathable film layer/apertured film layer laminate is then attached to a SMS nonwoven by thermal bonding. The resulting composite laminate is suitable for use as a breathable backsheet on an absorbent article.

The following examples are meant to be exemplary products and procedures only which aid in the understanding of the present invention. The inventive laminate was made according to the following examples.

EXAMPLE 1

Figure 7:
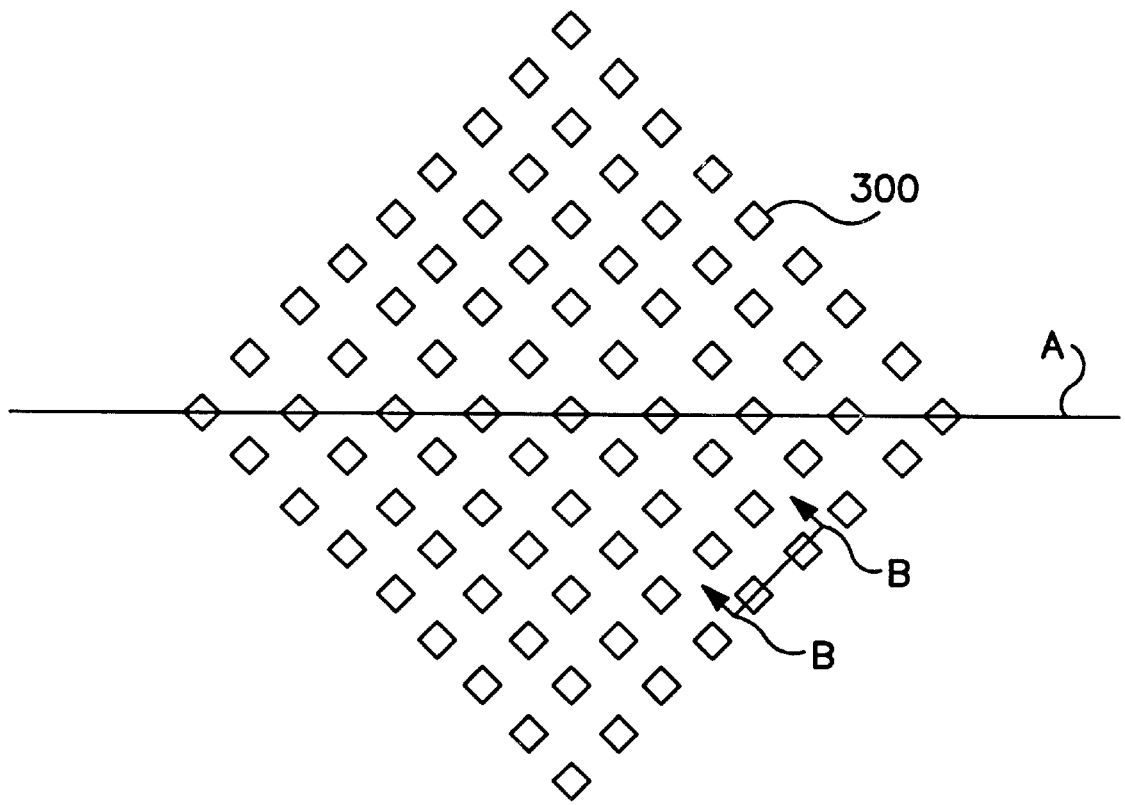
FIG. 7 is a top view of an aperturing pattern on a pattern roll that has been extended out in a flat horizontal plane and which may be utilized as a pattern to construct the apertured film that may be utilized in the present inventive laminate.
Figure 8:
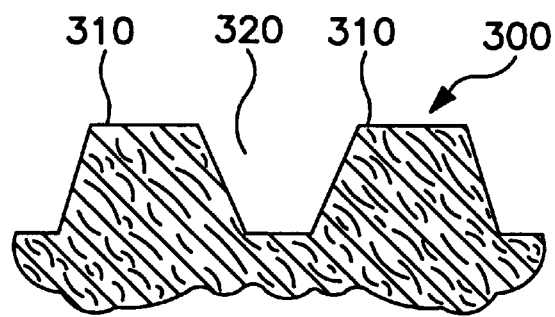
FIG. 8 is a cross-sectional view along line B—B in FIG. 7.

An apertured polyethylene film was constructed on an aperturing apparatus similar to that shown in FIG. 5. The apparatus employed had 24-inch diameter and 24-inch wide pattern and anvil rollers (although other diameters and widths would be acceptable). The particular pattern utilized to create the apertures in the film was a diamond pattern shown in FIG. 7. FIG. 7 shows a diamond pattern of aperturing protuberances 300. Line A indicates the horizontal axis of the pattern roller as if it were laid out in one horizontal plane. FIG. 8 illustrates a cross-section of the pattern roller arrangement along line B—B in FIG. 7. In particular, each protuberance 300 has a top surface 310 and a valley, or void, 320 which will created the apertured characteristics on the film. The bond area of the particular pattern roll used in the present example was 31% to 32% of the entire film surface area.

In making the apertured film, the speed of the pattern roller was set at 172 feet per minute (fpm) and the speed of the anvil roller was set at 116 fpm so that a differential speed ratio of 1.51 was obtained. The speed of the pull roll was set at 135 fpm and the winder speed was set at 158 fpm. The temperature of the pattern roll was set at 200° F. (93.3° C.) and the temperature of the anvil roll was set at 180° F. (82.2° C.). The nip pressure between the pattern and anvil rolls was set at 640 pounds per square inch (psi) on the operator's side and at 636 psi on the drive side.

A continuous low density polyethylene film containing titanium dioxide as an opacifier was subjected to the aperturing process at the process parameters described above by feeding the film through the nip formed by the pattern and anvil rollers. The actual temperature of the pattern roll during the process was 190° F. (87.8° C.) and the actual temperature of the anvil roll during the process was 178° F. (81.1° C.). These parameters produced an apertured film suitable for use in the present invention.

It should be appreciated that various methods may be employed for producing the apertured film and that the process parameters may be varied depending on the characteristics desired in the apertured film and the capabilities of the particular processing equipment being employed. For example, pattern roll speeds of 86 fpm to 450 fpm might be acceptable when coupled with anvil speeds of 77 fpm to 381 fpm to provide differential speed ratios of from about 1.11 to about 1.88. In addition, various set pattern roll and anvil roll temperatures may be utilized, ranging from about 180° F. (82.2° C.) to about 217° F. (102.8° C.). Nip pressures may vary, depending on the particular processing equipment, from 465 psi to 700 psi. Any number of various aperturing patterns may be utilized as well as a myriad of various types of pattern/anvil roller arrangements.

EXAMPLES 2–6

Five samples of the apertured film produced in Example 1 above were then coextruded with a layer of ethylene vinyl alcohol. A common extruder known as a NRM, 3.5" diameter extruder, having a length to diameter ratio of 24 to 1 was utilized for the process. The extruder had components that are well known in the art, such as a spin pump with a certain rotation, a 5-temperature barrel zone, and a die zone.

The EVA employed in the present examples was obtained from the Exxon Corporation and was sold under the designation Exxon 760.36. This particular EVA had a melt temperature of 400° F. (204.4° C.). The five apertured film samples were coated with different thicknesses of the EVA film during a coextrusion process.

The amount of EVA utilized on the five samples were as follows: 25 gsm (coextruded at a rate of 45 fpm); 15 gsm (coextruded at a rate of 70 fpm); 11.3 gsm (coextruded at a rate of 100 fpm); 10 gsm (coextruded at a rate of 113 fpm); and 9 gsm (coextruded at a rate of 125 fpm). The process conditions for Examples 2–6 were identical except for the line speed. Such process conditions included a melt pressure (also known as discharge pressure) at the spin pump of 280 psi; an amperage of 1.3 amps; a spin pump rotation of 5 rpm; a suction pressure upstream of the spin pump of 300 psi; barrel zone temperatures of 300° F. (148.9° C.), 350° F. (177.7° C.), 375° F. (190.6° C.), 385° F. (196.1° C.), and 400° F. (204.4° C.); and a die zone temperature of 425° F. (218.3° C.).

Two of the five breathable film/apertured film laminates were tested to determine their water vapor transmission rates. A vapor-pervious material will have a water vapor transmission rate, or WVTR, which is indicative of the ability of the material to allow vapor to pass through it.

A standard technique for determining the WVTR of a material is ASTM E96-80 and is as follows. Circular samples are cut from the test material. Test cups used for testing are cast aluminum, flanged, 2 inches deep and are equipped with a mechanical seal and a neoprene gasket. The cups are distributed by companies such as Thwing-Albert Instrument Company of Philadelphia, Pa. under the designation Vapometer cup #681. One hundred milliliters of distilled water is poured into each Vapometer cup, and each of the individual test samples are placed across the open top area of an individual cup. Screw-on flanges are tightened to form a seal along the edge of the cups leaving the associated test material exposed to the ambient atmosphere over a 62 millimeter diameter circular area an open, exposed area of about 30 cm$^2$). The cups are then weighed, placed on a tray in an upright position, and provided to a forced air oven set at 100° F. (37.8° C.). The oven is a constant temperature oven with external air circulating through to prevent water vapor from accumulating inside. A suitable oven is, for example, a Blue M Power-O-Matic 60 oven distributed by Blue M Electric Company of Blue Island, Ill. After 24 hours, the cups are removed from the oven and weighed. The WVTR value is calculated by multiplying the grams of weight loss over the 24-hour period by 7571 and dividing by 24. WVTR is then expressed in grams/square meters/24 hours (g/m$^2$/day).

A desirable WVTR for the purposes of the present invention would be at least 300 g/m$^2$/day. A preferred for using the inventive laminate on absorbent articles would be at least 1000 g/m$^2$/day. An even more preferred would be 2000 g/m$^2$/day. Obviously, the more breathable products will have a higher, which is more desirable in the presently described products.

The apertured film coated with EVA at 45 fpm (25 gsm) exhibited a of 494 g/m$^2$/day and the apertured film coated with EVA at 125 fpm (9 gsm) exhibited a of 1513 g/m$^2$/day.

EXAMPLES 7–11

Each of the five breathable film/apertured film laminates from Examples 2–6 above were then thermally bonded to a layer of nonwoven spunbond material having a basis weight of 0.5 osy. In these Examples, the apertured film side of the breathable film/apertured film laminate 40 was bonded to a surface of the nonwoven web as illustrated in FIG. 2.

To accomplish thermal bonding, the breathable film/apertured film laminate was placed on top of the spunbond web and subjected to a calendaring process. Calendaring processes are common in the industry and are generally performed by subjecting a substrate to an embossing nip formed by a pattern roll and an anvil roll. The set-up is nearly identical to the aperturing apparatus shown in FIG. 5, except that an additional unwind would be present to provide the second material (either the nonwoven web or the breathable polymer/apertured film layer) and the pattern roll would not have the protuberances.

In the particular calendaring process to which the present laminate was subjected, a nip pressure of 90 psi was employed. The temperature of the anvil roll in the calendaring process was set at 100° F. (37.8° C.) and the temperature of the pattern roll was set at 150° F. (65.6° C.) to achieve the thermally bonded breathable, apertured film/nonwoven laminate.

The resulting laminates exhibited the clothlike aesthetics of nonwoven materials while retaining the liquid-impermeable, vapor-pervious characteristics provided by the breathable film and apertured film layers.

Although a preferred embodiment of the invention has been described using specific terms, devices, and methods, such description is for illustrative purposes only. The words used are words of description rather than of limitation. It is to be understood that changes and variations may be made by those of ordinary skill in the art without departing from the spirit and scope of the present invention which is set forth in the following claims. In addition, it should be understood that aspects of the various embodiments may be interchanged, both in whole or in part.

What is claimed is:

1. An absorbent article comprising:
   a) an absorbent material; and
   b) a breathable, liquid-impermeable, vapor-pervious backsheet positioned adjacent to said absorbent material, said backsheet comprising
      a nonwoven web layer having a first surface and a second surface; a non-fibrous, apertured film layer having a first surface and a second surface; and
      a nonporous, breathable polymeric film layer having a first surface and a second surface,
         wherein one of said surfaces of said non-fibrous apertured film layer is bonded to one of said surfaces of said nonporous, breathable polymeric film layer to form a breathable film/polymeric film layer and said breathable film/polymeric film layer is bonded to one of said surfaces of said nonwoven web layer.

2. The absorbent article of claim 1 wherein the nonwoven web layer comprises a web chosen from the group consisting of spunbonded fiber webs, meltblown fiber webs, spunbonded/meltblown/spunbonded fiber webs, and bonded carded webs.

3. The absorbent article of claim 1 wherein said non-fibrous, apertured film layer comprises a polyolefin film.

4. The absorbent article of claim 1 wherein the backsheet has a water vapor transmission rate of at least 2000 g/m$^2$/days.

5. The absorbent article of claim 1 wherein said nonporous, breathable polymeric film layer comprises a polymer chosen from the group consisting of poly(vinyl alcohol), polyvinyl acetate, ethylene vinyl alcohol, polyurethane, ethylene methyl acrylate, and ethylene methyl acrylic acid.

6. The absorbent article of claim 1 wherein said second surface of said nonporous, breathable polymeric film layer is bonded to said first surface of said nonwoven web layer and said second surface of said non-fibrous, apertured film layer is bonded to said first surface of said nonporous, breathable polymeric film layer.

7. The absorbent article of claim 1 wherein said second surface of said non-fibrous, apertured film layer is bonded to said first surface of said nonwoven web layer and said second surface of said nonporous, breathable polymeric layer is bonded to said first surface of said non-fibrous, apertured film layer.

8. The absorbent article of claim 1 wherein said non-fibrous, apertured film layer has a thickness of from about 4 mils (0.01016 cm) to about 40 mils (0.1016 cm), said nonporous, breathable film layer has a thickness of from about 0.01 mils (8.478 gsm) to about 5 mils (0.0127 cm), and said nonwoven web layer has a basis weight of from about 0.25 osy (8.478 gsm) to about 5.0 osy (169.6 gsm).

9. The absorbent article of claim 1 wherein said non-fibrous, apertured film layer has a thickness of from about 10 to about 20 mils (0.0254 to about 0.0508 cm), said nonporous, breathable film layer has a thickness of from about 0.01 mils to about 1.0 mils ($2.54 \times 10^{-5}$ cm to about $2.54 \times 10^{-3}$ cm), and said nonwoven web layer has a basis weight of from about 0.25 osy (8.478 gsm) to about 5.0 osy (169.5 gsm).

10. The absorbent article of claim 1 wherein the backsheet has a water vapor transmission rate of at least 300 $g/m^2/$days.

11. The absorbent article of claim 1 wherein the backsheet has a water vapor transmission rate of at least 1000 $g/m^2/$days.

12. The absorbent article of claim 1 wherein the absorbent material further comprises:

a liquid-pervious top sheet joined to the backsheet; and wherein the absorbent material is an absorbent core sealed between the backsheet and the top sheet.

13. The absorbent article of claim 12 wherein said polyolefin is polyethylene.

14. The absorbent article of claim 12 wherein said article is an article chosen from the group consisting of diapers, incontinent garments, sanitary napkins, bedpads, and training pants.

15. The absorbent article of claim 12 wherein said backsheet has a water vapor transmission rate of at least 300 $g/m^2/day$.

16. The absorbent article of claim 12 wherein said backsheet has a water vapor transmission rate of at least 1000 $g/m^2/day$.

17. The absorbent article of claim 12 wherein said backsheet has a water vapor transmission rate of at least 2000 $g/m^2/day$.

18. An absorbent article comprising:

an absorbent material disposed between a breathable, liquid-impermeable backsheet and a liquid permeable topsheet, said backsheet comprising:

a breathable, liquid-impermeable, laminate comprising:

a) a breathable layer comprising a non-fibrous, apertured film and a nonporous, breathable polymeric film; and b) a nonwoven web layer, said breathable layer being bonded to said nonwoven web layer to form said breathable, liquid-impermeable, laminate.

19. The breathable, liquid impermeable, laminate of claim 18 wherein said breathable layer is bonded to said nonwoven web layer so that said nonporous, breathable polymeric film is positioned between said non-fibrous, apertured film and said nonwoven web.

20. The breathable, liquid impermeable, laminate of claim 18 wherein said breathable layer is bonded to said nonwoven web layer so that said non-fibrous, apertured film is positioned between said nonporous, breathable film and said nonwoven web.

* * * * *